(12) United States Patent
Guditi

(10) Patent No.: US 11,602,507 B2
(45) Date of Patent: Mar. 14, 2023

(54) EXTENDED RELEASE ORAL COMPOSITION OF MEMANTINE OR ITS SALT AND ITS PROCESS FOR THE PREPARATION

(71) Applicant: TRIKONA PHARMACEUTICALS PVT. LTD, Hyderabad (IN)

(72) Inventor: Venkata Sudarsan Guditi, Hyderabad (IN)

(73) Assignee: Trikona Pharmaceuticals PVT. LTD, Hyderabad (IN)

( * ) Notice: Subject to any disclaimer, the term of this patent is extended or adjusted under 35 U.S.C. 154(b) by 416 days.

(21) Appl. No.: 16/590,103

(22) Filed: Oct. 1, 2019

(65) Prior Publication Data
US 2020/0375921 A1    Dec. 3, 2020

(30) Foreign Application Priority Data

May 27, 2019 (IN) .............................. 201941020975

(51) Int. Cl.
*A61K 31/13* (2006.01)
*A61K 9/14* (2006.01)

(52) U.S. Cl.
CPC ................ *A61K 31/13* (2013.01); *A61K 9/14* (2013.01)

(58) Field of Classification Search
CPC ..................................................... A61K 31/13
See application file for complete search history.

(56) References Cited

U.S. PATENT DOCUMENTS

| | | | |
|---|---|---|---|
| 2,990,332 A | 6/1961 | Keating | |
| 4,221,778 A | 9/1980 | Raghunathan | |
| 4,859,461 A | 8/1989 | Chow et al. | |
| 4,894,239 A | 1/1990 | Nonamura et al. | |
| 5,382,601 A | 1/1995 | Nurnberg et al. | |
| 6,194,000 B1 | 2/2001 | Smith et al. | |
| 8,058,291 B2 | 11/2011 | Went et al. | |
| 8,062,667 B2 | 11/2011 | Mehta et al. | |
| 2003/0099711 A1 | 5/2003 | Meadows et al. | |

FOREIGN PATENT DOCUMENTS

| | | |
|---|---|---|
| DE | 2246037 | 4/1974 |
| WO | 2015/037019 | 3/2015 |

*Primary Examiner* — Barbara P Badio
(74) *Attorney, Agent, or Firm* — Shumaker & Sieffert, P.A.

(57) ABSTRACT

The present invention relates to oral extended release composition, comprising memantine or its pharmaceutically acceptable salt as an active ingredient, resin complexation ingredient, release retardant, extended release coating system and the composition further comprising diluents, viscosity increasing agents, glidants, sweeteners, stabilizing agents, preservatives and other pharmaceutically acceptable excipients, wherein the drug-resin complex and drug-resin complex matrix particulates and coated drug-resin complex particulates have the specific particle size range. The present invention also relates to a process for the preparation of memantine or its salt oral extended release composition comprising the steps of drug-resin complexation, matrix resinate/particulates preparation process followed by extended release coating. The present invention also relates to oral extended release composition comprising memantine or its pharmaceutically acceptable salt as an active ingredient and pharmaceutically acceptable excipients using extended release resin-complexation technology, further comprising additional active ingredient is in its immediate release form.

7 Claims, 1 Drawing Sheet

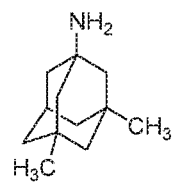

EXTENDED RELEASE ORAL COMPOSITION OF MEMANTINE OR ITS SALT AND ITS PROCESS FOR THE PREPARATION

This application claims the benefit of Indian Patent Application No. 201941020975 filed May 27, 2019, the entire content of which is incorporated herein by reference.

FIELD OF THE INVENTION

The present invention relates to oral extended release composition comprising memantine or its pharmaceutically acceptable salt as an active ingredient and pharmaceutically acceptable excipients using extended release resin-complexation technology.

The present invention also relates to oral extended release composition comprising memantine or its pharmaceutically acceptable salt as an active ingredient, resin complexation ingredient, release retardant, extended release coating system and other pharmaceutically acceptable excipients wherein the drug-resin complex and drug-resin complex matrix particles and coated drug-resin complex particles have the specific particle size range.

The present invention specifically relates to oral extended release composition, comprising memantine or its pharmaceutically acceptable salt as an active ingredient, resin complexation ingredient, release retardant, extended release coating system and other pharmaceutically acceptable excipients, wherein the composition further comprising diluents, viscosity increasing agents, glidants, sweeteners, stabilizing agents, preservatives and other pharmaceutically acceptable excipients.

The present invention specifically relates to a process for the preparation of memantine or its salt oral extended release composition comprising the steps of drug-resin complexation, matrix resinate/particulates preparation by aqueous granulation or extrusion/spheronization process followed by extended release coating, blending/granulation and packing.

The present invention also relates to oral extended release composition comprising memantine or its pharmaceutically acceptable salt as an active ingredient and pharmaceutically acceptable excipients using extended release resin-complexation technology, further comprising additional active ingredient in its immediate release form.

BACKGROUND OF THE INVENTION

Extended release oral dosage forms permit the sustained release of the active ingredient over an extended period of time in an effort to maintain therapeutically effective plasma levels over similarly extended time intervals, improve dosing compliance and to modify pharmacokinetic properties of the active ingredient. However, modulation of the release rate of an active ingredient does not necessarily ensure that long-lasting effective blood level concentrations will be consistently achieved or that the pharmacological effect will be based solely on the release of the drug.

Ion-exchange systems are advantageous for drugs that are highly susceptible to degradation by enzymatic process. However, the limitation is that the release rate is proportional to the concentration of the ions present in the area of administration. The release rate of drug can be affected by variability in diet, water intake and individual intestinal content.

Ion exchange resins are cross-linked synthetic high molecular weight solid water insoluble usually white or yellowish, fabricated from organic polymer (polyelectrolyte) having ionisable functional group. Complexes between IER and drugs are known as ion exchange resinates which is one of the attractive method for modified drug delivery system.

The major drawback of controlled release dosage form is dose dumping, resulting in increased risk of toxicity. The usage of Ion-exchange resins during the development of controlled release formulations plays a significant role because of their drug retarding properties and prevention of dose dumping. The drug resinates can also be used as a drug reservoir, which will change the drug release in hydrophilic polymer composition.

Memantine is an adamantane derivative chemically, 1-amino-3,5-dimethyladamantane, orally active NMDA receptor antagonist and it acts on the glutamatergic system by blocking NMDA receptors.

Memantine has a molecular formula of $C_{12}H_{21}N$ and has a molecular mass of 215.77 gm/mol (as hydrochloride) and 179.31 gm/mol (free base). It has a structural formula illustrated in FIG. 1.

Memantine appears as a white, almost odourless crystalline powder, highly soluble in water. Its pKa-value is 10.27 and shows a partition coefficient (log P) of 3.28. The active substance has two chiral centres but since there is a plane of symmetry between them, the molecule is not chiral and it exhibits only one polymorphic form.

Some patent literature describes the compositions of memantine or its pharmaceutically acceptable salt comprising impregnating agent, water-insoluble film-forming synthetic resin, ion-exchange resin, extended release coating wherein the composition release rates are different which includes immediate release portion and extended release portions.

U.S. Pat. No. 2,990,332 A discloses composition comprising adsorbed amphetamines onto a sulphonic acid cation exchange resin from which the drug is slowly and uniformly released by gastric and intestinal juices, a homogeneous pharmaceutical drug compound which will immediately release without the necessity of enteric coating its drug continuously over a long period of time. The release rate of amphetamine from the amphetamine-resin complex is not more than 50% in one hour by elution with simulated gastric juice and at least approximately 10% in three hours by elution.

German Patent No. DE 22 46 037 B2 discloses peroral drug with reduced absorbability, the active substance of which is adsorbed on to an ion exchange resin having a thin coating of a water-insoluble film-forming synthetic resin, characterized in that the loaded exchange resin particles having specific particle size, which are coated with a acrylic acid esters or methacrylic acid esters, which is modified with ammonium group copolymer. The release of the active substance is delayed by using the cellulose acetate phthalate as release retardant.

U.S. Pat. No. 4,221,778 A discloses the pharmaceutical preparation comprising ion exchange resin particles having a pharmacologically active drug absorbed thereon to form drug-resin complex particles, which resin particles have been treated with an impregnating agent in an amount sufficient to retard their rate of swelling in water, which are selected from the group consisting of polyethylene glycol, propylene glycol, mannitol, lactose and methylcellulose, wherein the treated particles have been subsequently coated with a water-permeable diffusion barrier. The pre-treatment of drug resin complex particles has enabled the effective application thereto of diffusion barrier coatings, resulting in the ability to effectively prolong the release of drugs from drug resin complexes.

U.S. Pat. No. 4,859,461 A discloses the process for enhancing the coatability of sulfonic acid cationic exchange resin particles which comprises contacting said particles with an aqueous solution containing from at least about 3% to about 20% by weight of an impregnating agent, based on the combined weight of the impregnating agent and the particles, said agent being selected from the group consisting of hydroxyl propyl methyl cellulose, hydroxyl propyl cellulose, sorbitol, hydroxyl propyl sorbitol, and polyvinylpyrrolidone, and thereafter individually coating said particles with a water permeable diffusion barrier.

U.S. Pat. No. 4,894,239 A discloses the sustained-release microcapsule preparation comprising an ion exchange resin which is about 6 to 16% cross-linked, drug adsorbed onto the ion exchange resin in an amount not less than 80% of its theoretical ion adsorption amount and coating the resulting ion exchange complex with a water-permeable polymer, wherein the water-permeable polymer is selected from the group consisting of polyacrylate, polymethacrylate, polyamide or acrylate-methacrylate copolymer.

U.S. Pat. No. 5,382,601 A discloses the solid pharmaceutical dosage forms containing memantine, which exhibit an extended two-phase release profile, with a portion of the drug being released immediately, followed by a sustained release of the remainder. The matrix of the formulation contains both a water-soluble and a water-insoluble salt of casein, preferably sodium and calcium caseinate.

U.S. Pat. No. 6,194,000 B1 discloses a method of preparing modified release N-methyl-D-aspartate (NMDA) receptor antagonists comprising 10% to 60% of immediate release form in association with 15% to 50% of controlled release form. The controlled release component is a sustained or extended release form is being coated with the pharmaceutically acceptable polymer such as ethyl cellulose, cellulose acetate butyrate, cellulose acetates, polymethacrylates containing quaternary ammonium groups or other pharmaceutically acceptable polymers, polyethylene glycol, hydroxypropyl cellulose, hydroxypropyl methyl cellulose, polyvinylpyrrolidone and polyvinyl alcohol.

U.S. Pat. No. 8,058,291 B2 discloses composition for treating and preventing CNS-related conditions comprising immediate release form of memantine and donepezil, wherein the composition is beads or pellets comprising an extended release coating filled in capsules, the extended release coating comprises an insoluble matrix polymer and a water soluble material.

U.S. Pat. No. 8,062,667 B2 discloses aqueous pharmaceutical suspension composition suitable for oral ingestion comprising particulate matrix comprising a particulate drug-ion exchange resin complex and a water insoluble polymer or copolymer, or hydrophilic polymer, said particulate matrix capable of passing through a specific mesh screen, said drug-ion exchange resin complex comprising a pharmaceutically acceptable drug bound to a pharmaceutically acceptable water insoluble ion exchange resin to form said drug-ion exchange resin complex, said ion exchange resin, aqueous dispersion and comprising (a) a polyvinylacetate polymer and (b) a stabilizer U.S. Pub. No. US 2003/0099711 A1 discloses an oral pharmaceutical composition comprising ion-exchange resin particles having particle sizes from 30 microns to about 500 microns; at least one pharmacologically active drug releasably bound to the particles to form drug-resin complexes, wherein the drug-resin complexes are coated with an aqueous based diffusion barrier which comprises from about 1% to about 60%, by weight of the resin particles, water-permeable, film-forming polymer.

PCT Pub No. WO 2015/037019 A2 discloses the modified release composition comprising plurality of modified release units comprising at least one anti-Alzheimer's agent, at least ion exchange resin and at least one release modifier, the drug resin complexes are impregnated with solvating agent, wherein the release modifier is present in the form of release modifying coating, the modified release composition further comprises an additional active agent which is delivered in an immediate or sustained release manner.

The commercially available product "Namenda" oral solution comprises memantine hydrochloride, sorbitol solution (70%), methylparaben, propylparaben, propylene glycol, glycerin, natural peppermint flavor #104, citric acid and sodium citrate, which is supplied in a strength equivalent to 2 mg of memantine hydrochloride in each mL.

Oral extended release suspension has the major drawback of flocculation/agglomeration problem with the use of polymethacrylic acid polymers in the extended release coating. The inventors of the present invention have developed extended release oral suspension by using polymethacrylic acid polymers by optimising the resinates in the matrix composition.

The present invention is an improvement over the prior art in that it delivers memantine hydrochloride in an extended release oral powder for suspension with extended release or modified release coating. The present invention relates to the extended release oral suspension of memantine or its salt, where memantine or its salt is in extended release which shows drug retarding properties and prevention of dose dumping of memantine or its salt in stomach up to 24 hours by utilizing existing technologies.

The present invention also relates to the oral extended release composition comprising memantine or its pharmaceutically acceptable salt as an active ingredient and pharmaceutically acceptable excipients using extended release resin-complexation technology, further comprising donepezil or its salt as additional active ingredient is in immediate release form and the composition provides the better effect for the treatment of CNS-related conditions, Alzheimer's disease and Parkinson's disease by administering oral extended release suspension composition of Memantine or its pharmaceutically acceptable salt and it may be used in combination with Donepezil or its salt.

OBJECTIVE OF INVENTION

The main objective of the present invention is to provide an oral extended release composition comprising memantine or its pharmaceutically acceptable salt as an active ingredient and pharmaceutically acceptable excipients using extended release resin-complexation technology.

Another objective of the present invention is to provide an oral extended release composition comprising memantine or its pharmaceutically acceptable salt as an active ingredient, resin complexation ingredient, release retardant, extended release coating system and other pharmaceutically acceptable excipients wherein the drug-resin complex and drug-resin complex matrix particles and coated drug-resin complex particles with specific particle size range.

Another objective of the present invention is to provide an oral extended release composition comprising memantine or its pharmaceutically acceptable salt as an active ingredient, resin complexation ingredient, release retardant, extended release coating system and other pharmaceutically acceptable excipients, wherein the composition further comprising diluents, viscosity increasing agents, glidants, sweeteners, stabilizing agents, preservatives and other pharmaceutically acceptable excipients.

Another objective of the present invention is to provide a process for the preparation of oral extended release composition comprising the steps of drug-resin complexation, matrix resinate/particulates preparation by aqueous granulation or extrusion/spheronization process followed by extended release coating, blending/granulation and packing.

Still another objective of the present invention is to provide oral extended release composition comprising memantine or its pharmaceutically acceptable salt as an active ingredient and pharmaceutically acceptable excipients using extended release resin-complexation technology, further comprising additional active ingredient in its immediate release form.

Yet another objective of the present invention is to provide better effect for the treatment of CNS-related conditions, Alzheimer's disease and Parkinson's disease by administering oral extended release suspension composition of Memantine or its pharmaceutically acceptable salt and it may used in combination with Donepezil or its salt.

SUMMARY OF INVENTION

Accordingly, the present invention provides oral extended release composition comprising memantine or its pharmaceutically acceptable salt as an active ingredient and pharmaceutically acceptable excipients using extended release resin-complexation technology.

In one embodiment, the present invention provides oral extended release composition comprising memantine or its pharmaceutically acceptable salt as an active ingredient, resin complexation ingredient, release retardant, extended release coating system and other pharmaceutically acceptable excipients wherein the composition drug-resin complex and drug-resin complex matrix particles and coated drug-resin complex particles with specific particle size range.

In one embodiment, the present invention provides oral extended release composition, comprising memantine or its pharmaceutically acceptable salt as an active ingredient, resin complexation ingredient, release retardant, extended release coating system and other pharmaceutically acceptable excipients, wherein the composition further comprising diluents, viscosity increasing agents, glidants, sweeteners, stabilizing agents, preservatives and other pharmaceutically acceptable excipients.

In another embodiment, the present invention provides oral extended release composition comprising drug-resin complex particles, matrix resinate/particulates and extended release coated drug resin matrix particles having particle size range at various stages.

In another embodiment, the present invention provides oral extended release composition comprising memantine or its pharmaceutically acceptable salt as an active ingredient and pharmaceutically acceptable excipients using extended release resin-complexation technology, further comprising additional active ingredient in its immediate release form.

In yet another embodiment, the present invention provides oral extended release composition comprising memantine or its pharmaceutically acceptable salt as an active ingredient and pharmaceutically acceptable excipients form using extended release resin-complexation technology, further comprising donepezil or its salt as additional active ingredient in its immediate release form.

In yet another embodiment, the present invention provides oral extended release composition comprising,
  5 to 15% (w/w) of memantine or its pharmaceutically acceptable salt,
  5 to 25% (w/w) of resin complexation ingredient,
  1 to 5% (w/w) of release retardant,
  5 to 26.5% (w/w) of extended release coating system, and
  15 to 65% (w/w) of other pharmaceutically acceptable excipients.

In yet another embodiment, the present invention provides oral extended release composition comprising,
  5 to 15% (w/w) of memantine or its pharmaceutically acceptable salt,
  5 to 25% (w/w) of resin complexation ingredient,
  1 to 5% (w/w) of release retardant,
  5 to 15% (w/w) of extended release coating polymer,
  0.1 to 3% (w/w) of plasticizing agent,
  1 to 8.5% (w/w) of anti-tacking agent, and
  15 to 65% (w/w) of other pharmaceutically acceptable excipients.

In yet another embodiment, the present invention provides oral extended release composition comprising,
  5 to 15% (w/w) of memantine or its pharmaceutically acceptable salt,
  5 to 25% (w/w) of resin complexation ingredient,
  1 to 5% (w/w) of one or more release retardant,
  5 to 15% (w/w) of extended release coating polymer,
  0.1 to 3% (w/w) of plasticizing agent,
  1 to 8.5% (w/w) of anti-tacking agent,
  0.1 to 5% (w/w) of additional active ingredient, and
  15 to 65% (w/w) of other pharmaceutically acceptable excipients.

In yet another embodiment, the present invention provides oral extended release composition comprising,
  5 to 15% (w/w) of memantine or its pharmaceutically acceptable salt,
  5 to 25% (w/w) of resin complexation ingredient,
  1 to 5% (w/w) of one or more release retardant,
  5 to 15% (w/w) of extended release coating polymer,
  0.1 to 3% (w/w) of plasticizing agent,
  1 to 8.5% (w/w) of anti-tacking agent,
  5 to 25% (w/w) of one or more viscosity increasing agents,
  1 to 5% (w/w) of stabilizing agents,
  20 to 35% (w/w) of diluents,
  1 to 5% (w/w) of glidants,
  0.01 to 5% (w/w) of sweeteners,
  1 to 5% (w/w) of preservatives,
  0.05 to 0.15% (w/w) of colorant,
  0.01 to 0.06% (w/w) of flavouring agent, and
  1 to 15% (w/w) of other pharmaceutically acceptable excipients.

In still another embodiment, the present invention provides oral extended release composition comprising,
  5 to 15% (w/w) of memantine or its pharmaceutically acceptable salt,
  5 to 25% (w/w) of sodium polystyrene sulfonate,
  1 to 5% (w/w) of polyvinyl pyrrolidone and/or copovidone,
  5 to 15% (w/w) of methacryclic acid copolymer,
  0.1 to 3% (w/w) of triethyl citrate,
  1 to 8.5% (w/w) of talc,
  5 to 25% (w/w) of sodium carboxy methyl cellulose and/or polyacrylic acid,
  1 to 5% (w/w) of colloidal silicon dioxide,
  20 to 35% (w/w) of mannitol,
  1 to 5% (w/w) of talc, 0.01 to 5% (w/w) of sucralose,
1 to 5% (w/w) of sodium benzoate,
0.05 to 0.15% (w/w) of iron oxide yellow,
0.01 to 0.06% (w/w) of orange flavour, and
1 to 15% (w/w) of other pharmaceutically acceptable excipients.

In still another embodiment, the present invention provides oral extended release composition comprising,
5 to 15% (w/w) of memantine or its pharmaceutically acceptable salt,
5 to 25% (w/w) of resin complexation ingredient,
1 to 5% (w/w) of one or more release retardant,
5 to 15% (w/w) of extended release coating polymer,
0.1 to 3% (w/w) of plasticizing agent,
1 to 8.5% (w/w) of anti-tacking agent,
0.1 to 5% (w/w) of additional active ingredient,
5 to 25% (w/w) of one or more viscosity increasing agents,
1 to 5% (w/w) of stabilizing agents,
20 to 35% (w/w) of diluents,
1 to 5% (w/w) of glidants,
0.01 to 5% (w/w) of sweeteners,
1 to 5% (w/w) of preservatives,
0.05 to 0.15% (w/w) of colorant,
0.01 to 0.06% (w/w) of flavouring agent, and
1 to 15% (w/w) of other pharmaceutically acceptable excipients.

In still another embodiment, the present invention provides oral extended release composition comprising,
5 to 15% (w/w) of memantine or its pharmaceutically acceptable salt,
5 to 25% (w/w) of sodium polystyrene sulfonate,
1 to 5% (w/w) of polyvinyl pyrrolidone and/or copovidone,
5 to 15% (w/w) of methacryclic acid copolymer,
0.1 to 3% (w/w) of triethyl citrate,
1 to 8.5% (w/w) of talc,
0.1 to 5% (w/w) of donepezil or its salt,
5 to 25% (w/w) of sodium carboxy methyl cellulose and/or polyacrylic acid,
1 to 5% (w/w) of colloidal silicon dioxide,
20 to 35% (w/w) of mannitol,
1 to 5% (w/w) of talc,
0.01 to 5% (w/w) of sucralose,
1 to 5% (w/w) of sodium benzoate,
0.05 to 0.15% (w/w) of Iron oxide yellow,
0.01 to 0.06% (w/w) of orange flavour, and
1 to 15% (w/w) of other pharmaceutically acceptable excipients.

In still another embodiment, the present invention provides the process for the preparation of memantine or its salt oral extended release composition comprising the steps of drug-resin complexation, matrix resinate/particulates preparation by aqueous granulation or extrusion/spheronization process followed by extended release coating, blending/granulation and packing.

In still another embodiment, the present invention provides a process for the preparation of oral extended release composition comprising the steps of:
a) drug-resin complexation,
b) drug-resin complex matrix preparation,
c) extended release coating, and
d) powder for oral suspension preparation.

In still another embodiment, the present invention provides a process for the preparation of oral extended release composition comprising the steps of:
a) drug-resin complexation: adding active ingredient to purified water in 1:22 ratio under stirring until clear solution obtained, adding cationic ion-exchange resin to obtained solution in 1:1.5 ratio under continuous stirring for 5 hours, filter the dispersion through #400 mesh and rinsing with purified water to obtain drug-resin complex, drying the drug-resin complex,
b) drug-resin complex matrix preparation: granulating the obtained drug-resin complex by adding release retardant in presence of solvent by aqueous granulation or extrusion/spheronization once or till the required particle size is achieved for obtaining the drug-resin matrix complex, drying the obtained granules, sifting the dried granules through #40 mesh to obtain the desired size of the drug-resin matrix granules,
c) extended release coating: drug-resin matrix granules obtained from the step (b) are coated with extended release coating system comprising extended release water insoluble/swellable polymers, plasticizer, anti-tacking agent and coating solvents obtaining extended release coated drug-resin complex matrix granules, and
d) powder for oral suspension preparation: sifting extended release coated drug resin matrix particulates, pre-granulated viscosity increasing agents with diuents, glidants, sweeteners, stabilizing agents, preservatives and other pharmaceutically acceptable excipients, followed by blending to obtain powder for oral suspension.

Still another embodiment, the present invention provides a process for the preparation of oral extended release composition comprising the steps of:
a) drug-resin complexation: adding active ingredient to purified water in 1:22 ratio under stirring until clear solution obtained, adding cationic ion-exchange resin to obtained solution in 1:1.5 ratio under continuous stirring for 5 hours, filter the dispersion through #400 mesh and rinsing with purified water to obtain drug-resin complex, drying the drug-resin complex,
b) drug-resin complex matrix preparation:
  i) adding release retardant to the drug-resin complex in presence of granulating solvent by aqueous granulation or extrusion/spheronization once or till the required particle size is achieved for obtaining the drug-resin matrix granules I, drying the obtained granules, sifting the dried granules through #40 mesh to obtain the desired size of the drug-resin matrix granules,
  ii) granulating the obtained drug-resin matrix granules I with the additional release retardant in presence of granulating solvent by aqueous granulation or extrusion/spheronization once or till the required particle size is achieved for obtaining the drug-resin matrix granules II, drying the obtained granules, sifting the dried granules through #24 mesh to obtain the desired size of the drug-resin matrix granules,
c) extended release coating: coating drug-resin matrix granules II obtained in step (b)(ii) with the extended release coating system comprising methacryclic acid copolymer or ethylcellulose, plasticizer, anti-tacking agent and coating solvents till the uniform extended release coated drug-resin complex granules obtained, and
d) powder for oral suspension preparation: sifting extended release coated drug resin matrix granules II, diluents, pre-granulated viscosity increasing agents with diuents, glidants, adding additional active ingredient directly either in powder form or granulated form with mannitol or polyacrylic acid in the extra-granular portion in blending step, further blending the obtained granules by adding sweeteners, stabilizing agents, preservatives and other pharmaceutically acceptable excipients followed by blending for obtaining the powder for oral suspension.

Still another embodiment, the present invention provides a process for the preparation of oral extended release composition comprising the steps of:
a) drug-resin complexation: adding memantine or its pharmaceutically acceptable salt to purified water in 1:22 ratio under stirring until clear solution obtained, adding sodium polystyrene sulfonate to obtained solution in 1:1.5 ratio under continuous stirring for 5 hours, filter the dispersion through #400 mesh and rinsing with purified water to obtain drug-resin complex, drying the drug-resin complex,
b) drug-resin complex matrix preparation:
  i) adding polyvinyl pyrrolidone to the drug-resin complex in presence of granulating solvent by aqueous granulation or extrusion/spheronization once or till the required particle size is achieved for obtaining the drug-resin matrix granules I, drying the obtained granules, sifting the dried granules through #40 mesh to obtain the desired size of the drug-resin matrix granules,
  ii) granulating the obtained drug-resin matrix granules I with the co-povidone in presence of granulating solvent by aqueous granulation or extrusion/spheronization once or till the required particle size is achieved for obtaining the drug-resin matrix granules II, drying the obtained granules, sifting the dried granules through #24 mesh to obtain the desired size of the drug-resin matrix granules,
c) extended release coating: coating the drug-resin matrix granules II obtained in step (b)(ii) with the extended release coating system comprising methacryclic acid copolymer or ethylcellulose, plasticizer, anti-tacking agent and coating solvents till the uniform extended release coated drug-resin complex granules obtained, and
d) powder for oral suspension preparation: blending the extended release coated drug resin complex granules II with pre-granulated sodium carboxy methyl cellulose and/or polyacrylic acid with mannitol powder grade and spray dried mannitol, and talc and drying to obtain the dried granules, adding additional active ingredient directly either in powder form or granulated form with mannitol or polyacrylic acid in the extra-granular portion in blending step, further blending the obtained granules by adding sweeteners, stabilizing agents, preservatives and other pharmaceutically acceptable excipients.

BRIEF DESCRIPTION OF DRAWING

FIG. 1 is a diagram of a structural formula of memantine having a molecular formula of $C_{12}H_{21}N$ and a molecular mass of 215.77 gm/mol (as hydrochloride) and 179.31 gm/mol (free base).

DETAILED DESCRIPTION OF THE INVENTION

The term "comprising", which is synonymous with "including", "containing", or "characterized by" here is defined as being inclusive or open-ended, and does not exclude additional, unrecited elements or method steps, unless the context clearly requires otherwise.

The present invention provides an oral extended release composition comprising memantine or its salt as an active ingredient and pharmaceutically acceptable excipients using extended release resin-complexation technology.

The term "active ingredients" of the present invention is used to treat various types of CNS-related disorders. Preferably used active ingredient is Memantine or its salt, which acts as an agonist at the dopamine $D_2$ receptor with equal or slightly higher affinity than to the NMDA receptors, and it is also used to treat Alzheimer's disease, in combination with the additional active ingredient selected from cholinesterase inhibitors which is donepezil or its salt.

The present invention provides an oral extended release composition comprising memantine or its salt as an active ingredient, sodium polystyrene sulfonate as resin complexation ingredient, polyvinyl pyrrolidone alone or in combination with copovidone as release retardant, methacryclic acid copolymer as extended release coating polymer, triethyl citrate as plasticizer, talc as anti-tacking agent and isopropyl alcohol and purified water as coating solvent system in the extended release coating system and other pharmaceutically acceptable excipients.

The present invention provides an oral extended release composition, wherein the powder for oral suspension composition further comprising mannitol in all grades as diluent, sodium carboxy methyl cellulose alone or in combination with polyacrylic acid as viscosity increasing agents, talc as glidant, sodium benzoate as preservative, colloidal silicon dioxide as stabilizing agent, Iron oxide yellow as coloring agent, sucralose as sweetener, orange flavour as flavoring agent and other pharmaceutically acceptable excipients.

The present invention also provides a process for the preparation of oral extended release composition comprising the steps of drug-resin complexation, matrix resinates/particulates preparation by aqueous granulation or extrusion/spheronization process followed by extended release coating, blending/granulation and packing.

The particle size of the drug-resin complex in the extended release composition ranges from 40 to 250 μm, preferably in the range of 40 and 150 μm. The D(90) of the drug-resin complex is not more than 250 μm.

The particle size of the drug-resin matrix complex in the extended release composition ranges from 50 to 800 μm, preferably in the range of 50 and 300 μm. The D(90) of the drug-resin matrix complex is not more than 800 μm.

The particle size of the extended release coated drug-resinate matrix complex in the extended release composition ranges from 100 to 1000 μm, preferably in the range of 100 and 500 μm. The D(90) of the coated drug-resin matrix complex is not more than 1000 μm.

The term "active ingredients" of the present invention is used to treat dementia related to Alzheimer's disease. Preferably used active ingredient is memantine, is NMDA receptor antagonist acts by persistent activation of central nervous system N-methyl-D-aspartate (NMDA) receptors by the excitatory amino acid glutamate has been hypothesized to contribute to the symptomatology of Alzheimer's disease. Memantine is postulated to exert its therapeutic effect through its action as a low to moderate affinity uncompetitive (open-channel) NMDA receptor antagonist which binds preferentially to the NMDA receptor-operated cation channels.

The concentration of active ingredient used in the oral extended release composition of present invention is from 5% to 15% (w/w). Most preferably used concentration of active ingredient is from 8.0% to 10.50% (w/w).

The active ingredients additionally used in the present invention include donepezil or its salt.

The concentration of additional active ingredient used in the oral extended release composition of present invention is from 0.1% to 5% (w/w). Most preferably used concentration of additional active ingredient is from 3.0% to 3.9% (w/w).

Ion Exchange Resins:

Ion-exchange resins are water-insoluble and comprise a preferably pharmacologically inert organic and/or inorganic matrix containing functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g. modified cellulose and dextrans). The inorganic matrix preferably comprises silica gel modified by the addition of ionic groups. Covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups.

Typically the size of the ion-exchange particles is from about 5 microns to about 750 microns, preferably the particle size is within the range of about 40 microns to about 250 microns for liquid dosage forms although particles up to about 1,000 micron can be used for solid dosage forms, e.g., powder, tablets and capsules. Particle sizes substantially below the lower limit are generally difficult to handle in all steps of the processing. Generally, uncoated drug-ion exchange resin particles of the invention will tend to be at the lower end of this range, whereas coated drug-ion exchange resin particles of the invention will tend to be at the higher end of this range. However, both uncoated and coated drug-ion exchange resin particles may be designed within this size range.

Ion Exchange Resins are Mainly of Two Categories:
(a) cationic exchange resins,
(b) anionic exchange resins.

The oral extended release composition according to the invention resin-complexation ingredient is selected form cationic exchange resins and anionic exchange resins those that exchange positive ions, called cation exchange resins, and those that exchange negative ions, called anion exchange resins.

Anion exchange resins are cholestyramine resin and styrene divinyl benzene, cholestyramine resin is a strong base type 1 anion exchange resin powder with a polystyrene matrix and quarternary ammonium functional groups. A commercially available Cholestyramine resins is PUROLITE™ A430MR resin, another pharmaceutical grade cholestyramine resin is available as DUOLITE™ AP143/1094 as having a particle size in the range of 95%, less than 100 microns and 40%, less than 50 microns.

Cation exchange resins, e.g., AMBERLITE IRP-69, are particularly well suited for use with drugs and other molecules having a cationic functionality, including e.g., Kyron T-154 (sodium polystyrene sulfonate), Kyron T-114, Kyron T-134 (polacrilin potassium), Kyron T-159, Kyron T-123. The resins selected from the polystyrene sulfonates are polymers derived from polystyrene by the addition of sulfonate functional groups. The resin particles are strong acidic cation exchange resins, selected from the group consisting of polistirex, polacrilex, polacrilin or mixtures thereof.

Preferably, the resin complexation ingredient used in the extended release suspension composition is a cation exchange resin which is sodium polystyrene sulfonate.

The concentration of resin-complexation ingredient used in the oral extended release composition of present invention is from 5% to 25% (w/w). Most preferably used concentration of resin-complexation ingredient is from 12% to 21% (w/w). wherein, the ratio of resin complexation ingredient with respect to active ingredient in the present invention is in the range of 0.5:1 to 3.5:1, most preferably, 1:1 to 3:1.

The oral extended release composition according to the present invention comprise release retardant which includes polyvinyl pyrrolidone which can be in different viscosity ranges/grades, polyvinyl acetate polymer or a mixture of polymers containing same, copovidone, cellulose acetates, ethylcellulose polymers, acrylic based polymers or copolymers, cellulose phthalate, acrylic polymers from the methacrylic acid family may include, e.g., a copolymer comprising ethyl acrylate and methyl methacrylate, which are largely pH-independent polymers or any combination of water-insoluble polymers or polymer systems. Preferably, the release retardant used in the extended release suspension composition is polyvinyl pyrrolidone and its different viscosity ranges/grades and/or combination with co-povidone.

The concentration of release retardant used in the oral extended release composition of present invention is from 1% to 5% (w/w). Most preferably used concentration of release retardant is from 1.15% to 2.65% (w/w). The ratio of release retardant with respect to active ingredient in the present invention is in the range from 0.5:10 to 5:10, most preferably 1:10 to 4:10.

Extended Release Coating System

Extended release coating system includes the water insoluble/swellable extended release polymer, plasticizer, anti-tacking agent and coating solvents.

The oral extended release composition according to the present invention comprise water insoluble/swellable extended release coating polymer which includes cellulose acetate phthalate, cellulose acetate trimellitate, hydroxypropyl methylcellulose phthalate, polyvinyl acetate phthalate, ethyl cellulose, carboxymethylethylcellulose, co-polymerized methacrylic acid/methacrylic acid methyl esters, co-polymerized methacrylic acid/acrylic acid ethyl esters, or mixtures thereof. Preferably, methacrylic acid/acrylic acid ethyl esters are used in the extended release coating polymer in the coating system.

Methacryclic acid copolymer and its grades include Eudragit RLPO and RSPO, having quaternary ammonium groups, are water insoluble, but swellable/permeable polymers which are suitable for the sustained release film coating applications.

The concentration of extended release coating polymer used in the oral extended release composition of present invention is from 5% to 15% (w/w). Most preferably used concentration of extended release coating polymer is from 6.2% to 13.89% (w/w). Further, the ratio of extended release coating polymer with respect to active ingredient in the present invention is in the range from 0.5:1 to 2.5:1.

The oral extended release composition according to the present invention comprise plasticizing agents or plasticizers which includes but are not limited to triethyl citrate, glycerols, glycerine, sorbitol, propylene glycol, polyethylene glycol, acetylated monoglycerides and alkyl citrates. Preferably, the plasticizing agent used in the extended release suspension composition is triethyl citrate.

The concentration of plasticizing agents or plasticizers used in the oral extended release composition of present invention is from 0.1% to 3% (w/w). Most preferably used concentration of plasticizing agents or plasticizers is from 0.5% to 2.35% (w/w). The ratio of plasticizer with respect to the active ingredient in the present invention is in the range from 0.2:10 to 3:10, most preferably 0.5:10 to 2:10.

The oral extended release composition according to the present invention comprise anti-tacking agents which includes talc, glyceryl monostearate or any combination thereof. Preferably, the anti-tacking agent used in the extended release suspension composition is talc.

The concentration of anti-tacking agents used in the oral extended release composition of present invention is from 1% to 8.5% (w/w). Most preferably used concentration of anti-tacking agents is from 1.25% to 7.5% (w/w). The ratio of anti tacking agent with respect to active ingredient in the present invention is in the range from 0.2:10 to 2:10, most preferably, it is 0.4:10 to 1.2:10.

The oral extended release composition according to the present invention, further comprising viscosity increasing agents, diluents, glidants, sweeteners, stabilizing agents, preservatives, flavouring agents, colorants and other pharmaceutically acceptable excipients.

The oral extended release composition according to the present invention comprise viscosity increasing agents which include, but not limited to sodium carboxy methyl cellulose, carbomer, carbopol or crosslinked polyacrylic acid polymers, gellan gum, xanthan gum and carrageenan. Preferably, the viscosity increasing agents used in the extended release suspension composition is sodium carboxy methyl cellulose and polyacrylic acid.

The concentration of viscosity increasing agents used in the oral extended release composition of present invention is from 5% to 25% (w/w). Most preferably used concentration of viscosity increasing agents is from 7.0% to 21.5% (w/w).

The oral extended release composition according to the present invention comprise stabilizing agents which include but not limited to calcium carbonate, colloidal silicone dioxide, microcrystalline cellulose, kaolin, activated charcoal, dibasic calcium phosphate, Bentonite, natural clay, activated alumina, zeolites and the like. Preferably, the stabilizing agent used in the extended release suspension composition is colloidal silicone dioxide.

The concentration of stabilizing agents used in the oral extended release composition of present invention is from 1% to 5% (w/w). Most preferably used concentration of stabilizing agents is from 2.94% to 3.7% (w/w).

The oral extended release composition according to the present invention comprise diluents such as microcrystalline cellulose, powdered cellulose, lactose (anhydrous or monohydrate), compressible sugar, fructose, dextrans, other sugars such as all grades of mannitol, sorbitol, lactitol, saccharose or a mixture thereof, citric acid anhydrous, siliconised microcrystalline cellulose, calcium hydrogen phosphate, calcium carbonate. Preferably, the diluent used in the extended release suspension composition is all grades of mannitol.

The concentration of diluents used in the oral extended release composition of present invention is from 20% to 35% (w/w). Most preferably used concentration of diluents is from 28.5% to 34.9% (w/w).

The oral extended release composition according to the present invention comprise glidants which include, but are not limited to talc, fumed silica, magnesium stearate, stearic acid, kaolin, magnesium trisilicate. Preferably, the glidant used in the extended release suspension composition is talc.

The concentration of glidants used in the oral extended release composition of present invention is from 1% to 5% (w/w). Most preferably used concentration of glidants is from 1.45% to 2.86% (w/w).

The oral extended release composition according to the present invention comprise sweetening agents/sweeteners which include, but are not limited to saccharin, aspartame, sucralose, thaumatin, acesulfame potassium, stevioside, stevia extract, paramethoxy cinnamic aldehyde, neohesperidyl dihydrochalcone and perillartine. Preferably, the sweetener used in the extended release suspension composition is sucralose.

The concentration of sweetening agents/sweeteners used in the oral extended release composition of present invention is from 0.01% to 5% (w/w). Most preferably used concentration of sweetening agents/sweeteners is from 0.85% to 1.15% (w/w).

The oral extended release composition according to the present invention comprise preservatives which include, parabens include methyl paraben, propyl paraben, benzyl alcohol, sodium benzoate, phenol, benzalkonium chloride, thimerosal, chlorobutanol, benzoic acid, sodium bisulfate, and sodium proprionate. Preferably, the preservative used in the extended release suspension composition is sodium benzoate.

The concentration of preservatives used in the oral extended release composition of present invention is from 1% to 5% (w/w). Most preferably used concentration of preservatives is from 2.5% to 3.35% (w/w).

The oral extended release composition according to the present invention comprise flavors which include, synthetic flavor oils and flavoring aromatics and/or natural oils, extracts from plant leaves, flowers, fruits, and so forth and combinations thereof. Suitable oils include, for example, cinnamon oil, oil of wintergreen, peppermint oils, clove oil, bay oil, anise oil, eucalyptus oil, thyme oil, cedar leaf oil, oil of nutmeg, oil of sage, oil of bitter almonds, cassia oil, vanilla, citrus oil (e.g., lemon, orange, grape, lime, grapefruit), citric acid, menthol, glycine, orange powder, cream, chocolate, mocha, spearmint, cola, apple, apricot, banana, cherry, peach, pear, pineapple, plum, raspberry and strawberry. Preferably, the flavor used in the extended release suspension composition is orange flavour.

The concentration of flavoring agents used in the oral extended release composition of present invention is from 0.01% to 0.06% (w/w). Most preferably used concentration of flavoring agents is from 0.29% to 0.37% (w/w).

The oral extended release composition according to the present invention comprise colouring agents which include, but are not limited to FD&C dyes and pigments, iron oxide yellow, mica, magnesium carbonate, calcium carbonate, magnesium silicate, magnesium aluminum silicate, silica, titanium dioxide, zinc oxide, is red, yellow, brown and black iron oxides, ferric ammonium ferrocyanide, manganese violet, ultramarine, titaniated mica, bismuth oxychloride, and mixtures thereof. Preferably, the colouring agent used in the extended release suspension composition is iron oxide yellow.

The concentration of colouring agents used in the oral extended release composition of present invention is from 0.05% to 0.15% (w/w). Most preferably used concentration of colouring agents is from 0.85% to 0.11% (w/w).

The oral extended release composition according to the present invention comprise solvents used for granulation which include, organic or inorganic solvent or mixtures thereof selected from isopropyl alcohol (IPA), acetone, ethanol, dichloromethane, purified water and mixtures thereof. The preferred granulation solvent is purified water and the preferred coating solvents are isopropyl alcohol and purified water.

The following examples describes the nature of the invention and are given only for the purpose of illustrating the present invention in more detail and are not limitative and relate to solutions, which have been particularly effective on bench scale.

EXAMPLES

Example 1

| S. NO. | Ingredients | mg/unit | Percentage |
|---|---|---|---|
| 1. | Memantine HCl | 28.0 | 8.02 |
| 2. | Sodium polystyrene sulfonate | 70.0 | 20.04 |
| 3. | Purified water | Q.s | — |
|  | Drug resin complex | 98.0 | — |
| 4. | Drug complex | 98.0 | — |
| 5. | Polyvinyl pyrrolidone | 7.5 | 2.15 |
| 6. | Purified water | Q.s | — |
|  | Drug resin complex matrix | 105.5 | — |
| 7. | Drug resin complex matrix | 105.50 | — |
| 8. | Methacryclic acid copolymer | 18.200 | 5.21 |
| 9. | Methacryclic acid copolymer | 3.64 | 1.04 |
| 10. | Triethyl citrate | 4.4 | 1.26 |
| 11. | Talc | 5.5 | 1.57 |
| 12. | Isopropyl alcohol | Q.s | — |
| 13. | Purified water | Q.s | — |
|  | ER Coated particulates | 137.0 | — |
| 14. | Sodium carboxy methyl cellulose | 75.0 | 21.48 |
| 15. | Talc | 10.0 | 2.86 |
| 16. | Sodium benzoate | 9.0 | 2.58 |
| 17. | Colloidal silicon dioxide | 11.0 | 3.15 |
| 18. | Citric acid anhydrous | 100.0 | 28.63 |
| 19. | Iron oxide yellow | 3.0 | 0.86 |
| 20. | Sucralose | 3.0 | 0.86 |
| 21. | Orange flavour | 1.0 | 0.29 |
|  | Powder for Suspension (per unit) | 349.24 mg | 100.0 |

Example 2

| S. NO. | Ingredients | mg/unit | Percentage |
|---|---|---|---|
| 1. | Memantine HCl | 28.0 | 8.24 |
| 2. | Sodium polystyrene sulfonate | 70.0 | 20.59 |
| 3. | Purified water | Q.s | — |
|  | Drug resin complex | 98.0 | — |
| 4. | Drug resin complex | 98.0 | — |
| 5. | Polyvinyl pyrrolidone | 7.6 | 2.24 |
| 6. | Purified water | Q.s | — |
|  | Drug resin complex matrix | 105.6 | — |
| 7. | Drug resin complex matrix | 105.6 | — |
| 8. | Methacryclic acid copolymer | 33.39 | 9.82 |
| 9. | Methacryclic acid copolymer | 6.68 | 1.96 |
| 10. | Triethyl citrate | 7.98 | 2.35 |
| 11. | Talc | 10.02 | 2.95 |
| 12. | Isopropyl alcohol | Q.s | — |
| 13. | Purified water | Q.s | — |
|  | ER Coated particulates | 163.6 | — |
| 14. | Sodium carboxy methyl cellulose | 50.0 | 14.71 |
| 15. | Talc | 5.00 | 1.47 |
| 16. | Sodium benzoate | 9.00 | 2.65 |
| 17. | Colloidal silicon dioxide | 10.00 | 2.94 |
| 18. | Iron oxide yellow | 0.30 | 0.09 |
| 19. | Sucralose | 3.00 | 0.88 |
| 20. | Orange flavour | 1.00 | 0.29 |
| 21. | Mannitol | 98.03 | 28.83 |
|  | Powder for Suspension (per unit) | 340.00 mg | 100.0 |

Example 3

| S. NO. | Ingredients | mg/unit | Percentage |
|---|---|---|---|
| 1. | Memantine HCl | 28.00 | 9.82 |
| 2. | Sodium polystyrene sulfonate | 42.00 | 14.74 |
| 3. | Purified water | Q.s | — |
|  | Drug resin complex | 70.0 | — |
| 4. | Drug resin complex | 70.0 | — |
| 5. | Polyvinyl pyrrolidone | 7.2 | 2.53 |
| 6. | Purified water | Q.s | — |
|  | Drug resin complex matrix | 77.2 | — |
| 7. | Drug resin complex matrix | 77.2 | — |
| 8. | Methacryclic acid copolymer | 17.76 | 6.23 |
| 9. | Methacryclic acid copolymer | 3.55 | 1.25 |
| 10. | Triethyl citrate | 4.25 | 1.49 |
| 11. | Talc | 5.33 | 1.87 |
| 12. | Isopropyl alcohol | Q.s | 0.00 |
| 13. | Purified water | Q.s | — |
|  | ER Coated particulates | 108.1 | — |
| 14. | Sodium carboxy methyl cellulose | 50.00 | 17.54 |
| 15. | Talc | 5.00 | 1.75 |
| 16. | Sodium benzoate | 9.00 | 3.16 |
| 17. | Colloidal silicon dioxide | 10.00 | 3.51 |
| 18. | Iron oxide yellow | 0.30 | 0.11 |
| 19. | Sucralose | 3.00 | 1.05 |
| 20. | Orange flavour | 1.00 | 0.35 |
| 21. | Mannitol | 98.61 | 34.60 |
|  | Powder for Suspension (per unit) | 285.0 mg | 100.0 |

Example 4

| S. NO. | Ingredients | mg/unit | Percentage |
|---|---|---|---|
| 1. | Memantine HCl | 28.0 | 9.3 |
| 2. | Sodium polystyrene sulfonate | 42.0 | 14.0 |
| 3. | Purified water | Q.s | — |
|  | Drug resin complex | 70.0 | — |
| 4. | Polyvinyl pyrrolidone | 3.54 | 1.2 |
| 5. | Purified water | Q.s | — |
|  | Drug resin complex matrix | 73.54 | — |
| 6. | Drug resin complex matrix | 73.54 | — |
| 7. | Methacryclic acid copolymer | 29.24 | 9.7 |
| 8. | Methacryclic acid copolymer | 2.89 | 1.0 |
| 9. | Triethyl citrate | 3.21 | 1.1 |
| 10. | Talc | 16.06 | 5.4 |
| 11. | Isopropyl alcohol | Q.s | 0.0 |
| 12. | Purified water | Q.s | 0.0 |
|  | ER Coated particulates | 125.0 | — |
| 13. | Sodium carboxy methyl cellulose | 50.0 | 16.7 |
| 14. | Talc | 5.00 | 1.7 |
| 15. | Sodium benzoate | 9.00 | 3.0 |
| 16. | Colloidal silicon dioxide | 10.00 | 3.3 |
| 17. | Iron oxide yellow | 0.30 | 0.1 |

-continued

| S. NO. | Ingredients | mg/unit | Percentage |
|---|---|---|---|
| 18. | Sucralose | 3.00 | 1.0 |
| 19. | Orange flavour | 1.00 | 0.3 |
| 20. | Mannitol | 96.76 | 32.3 |
| | Powder for Suspension (per unit) | 300.0 mg | 100.0 |

Manufacturing Process for Extended Release Oral Suspension Preparation:

Oral extended release suspension composition preparation includes the steps of:

a) drug-resin complexation: memantine or its pharmaceutically acceptable salt was added to purified water in 1:22 ratio under stirring until clear solution obtained, sodium polystyrene sulfonate was added to obtained solution in 1:1.5 ratio under continuous stirring for 5 hours, filtered the dispersion through #400 mesh and rinsing with purified water to obtain drug-resin complex, drying to obtain dried drug-resin complex, b) drug-resin complex matrix preparation: polyvinyl pyrrolidone was added to the drug-resin complex in presence of granulating solvent by aqueous granulation or extrusion/spheronization once or till the required particle size is achieved for obtaining the drug-resin matrix granules I, drying to the obtain the dried granules, the dried granules were sifted through #40 mesh to obtain the desired size of the drug-resin matrix granules, c) extended release coating: drug-resin matrix granules obtained in step (b) were coated with the extended release coating comprising extended release water insoluble/swellable polymers, plasticizer, anti-tacking agent and coating solvents till the uniform extended release coated drug-resin complex granules obtained, and d) powder for oral suspension preparation: sifting extended release coated drug resin matrix particulates, pre-granulated viscosity increasing agents with diuents, glidants, sweeteners, stabilizing agents, preservatives and other pharmaceutically acceptable excipients, followed by blending to obtain powder for oral suspension.

Example 5

| S. No. | Ingredients | mg/unit | Percentage |
|---|---|---|---|
| 1. | Memantine HCl | 28.0 | 8.89 |
| 2. | Sodium polystyrene sulfonate | 42.0 | 13.33 |
| 3. | Purified water | Q.s | — |
| | Drug resin complex | 70.0 | — |
| 4. | Drug resin complex | 70.0 | — |
| 5. | Polyvinyl pyrrolidone | 2.1 | 0.67 |
| 6. | Copovidone | 2.9 | 0.92 |
| 7. | Purified water | Q.s | — |
| | Drug resin complex matrix | 75.0 | — |
| 8. | Drug resin complex matrix | 75.0 | — |
| 9. | Methacrylic acid copolymer | 29.85 | 9.48 |
| 10. | Methacrylic acid copolymer | 2.95 | 0.94 |
| 11. | Triethyl citrate | 3.28 | 1.04 |
| 12. | Talc | 16.40 | 5.21 |
| 13. | Isopropyl alcohol | Q.s | — |
| 14. | Purified water | Q.s | — |
| | ER Coated particulates | 127.5 | — |
| 15. | Sodium carboxy methyl cellulose | 50.00 | 15.87 |
| 16. | Talc | 5.00 | 1.59 |
| 17. | Sodium benzoate | 9.00 | 2.86 |
| 18. | Colloidal silicon dioxide | 10.00 | 3.17 |
| 19. | Iron oxide yellow | 0.30 | 0.10 |
| 20. | Sucralose | 3.00 | 0.95 |
| 21. | Orange flavour | 1.00 | 0.32 |
| 22. | Mannitol | 22.22 | 7.05 |
| 23. | Mannitol | 75.00 | 23.80 |
| 24. | Poly acrylic acid | 12.00 | 3.80 |
| | Powder for Suspension (per unit) | 315.00 mg | 100.0 |

Example 6

| S. NO. | Ingredients | mg/unit | Percentage |
|---|---|---|---|
| 1. | Memantine HCl | 28.0 | 9.03 |
| 2. | Sodium polystyrene sulfonate | 42.0 | 13.54 |
| 3. | Purified water | Q.s | Qs |
| | Drug resin complex | 70.0 | — |
| 4. | Drug resin complex | 70.0 | — |
| 5. | Polyvinyl pyrrolidone | 2.10 | 0.68 |
| 6. | CoPovidone | 2.88 | 0.93 |
| 7. | Purified water | Q.s | — |
| | Drug resin complex matrix | 74.98 | — |
| 8. | Drug resin complex matrix | 74.98 | — |
| 9. | Methacrylic acid copolymer | 25.56 | 8.25 |
| 10. | Methacrylic acid copolymer | 2.56 | 0.83 |
| 11. | Triethyl citrate | 2.81 | 0.91 |
| 12. | Talc | 14.06 | 4.54 |
| 13. | Isopropyl alcohol | Q.s | — |
| 14. | Purified water | Q.s | — |
| | ER Coated particulates | 120.0 | — |
| 15. | Sodium carboxy methyl cellulose | 50.00 | 16.13 |
| 16. | Talc | 5.00 | 1.61 |
| 17. | Sodium benzoate | 9.00 | 2.90 |
| 18. | Colloidal silicon dioxide | 10.00 | 3.23 |
| 19. | Iron oxide yellow | 0.30 | 0.10 |
| 20. | Sucralose | 3.00 | 0.97 |
| 21. | Orange flavour | 1.00 | 0.32 |
| 22. | Mannitol (Spray dried) | 39.2 | 12.65 |
| 23. | Mannitol (Powder grade) | 62.5 | 20.16 |
| 24. | Poly acrylic acid | 10.0 | 3.21 |
| | Powder for Suspension (per unit) | 310.0 mg | 100.0 |

Example 7

| S. NO. | Ingredients | mg/unit | Percentage |
|---|---|---|---|
| 1. | Memantine HCl | 28.0 | 10.37 |
| 2. | Sodium polystyrene sulfonate | 42.0 | 15.56 |
| 3. | Purified water | Q.s | Qs |
| | Drug resin complex | 70.0 | — |
| 4. | Drug resin complex | 70.0 | — |
| 5. | Polyvinyl pyrrolidone | 2.10 | 0.78 |
| 6. | Copovidone | 2.9 | 1.07 |
| 7. | Purified water | Q.s | — |
| | Drug resin complex matrix | 74.98 | — |
| 8. | Drug resin complex matrix | 74.98 | — |
| 9. | Methacrylic acid copolymer | 34.1 | 12.63 |
| 10. | Methacrylic acid copolymer | 3.40 | 1.26 |

-continued

| S. NO. | Ingredients | mg/unit | Percentage |
|---|---|---|---|
| 11. | Triethyl citrate | 3.75 | 1.39 |
| 12. | Talc | 18.75 | 6.94 |
| 13. | Isopropyl alcohol | Q.s | — |
| 14. | Purified water | Q.s | — |
|  | ER Coated particulates | 135.0 |  |
| 15. | ER Coated particulates | 135.0 | — |
| 16. | Sodium carboxy methyl cellulose | 10.00 | 3.70 |
| 17. | Talc | 5.00 | 1.85 |
| 18. | Sodium benzoate | 9.00 | 3.33 |
| 19. | Colloidal silicon dioxide | 10.00 | 3.70 |
| 20. | Iron oxide yellow | 0.30 | 0.11 |
| 21. | Sucralose | 3.00 | 1.11 |
| 22. | Orange flavour | 1.00 | 0.37 |
| 23. | Mannitol (Spray dried) | 20.00 | 7.41 |
| 24. | Mannitol (Powder grade) | 64.7 | 23.96 |
| 25. | Poly acrylic acid | 12.0 | 4.44 |
|  | Powder for Suspension (per unit) | 270.0 mg | 100.0 |

Example 8

| S. NO. | Ingredients | mg/unit | Percentage |
|---|---|---|---|
| 1. | Memantine HCl | 28.0 | 10.0 |
| 2. | Sodium polystyrene sulfonate | 42.0 | 15.0 |
| 3. | Purified water | Q.s | Qs |
|  | Drug resin complex | 70.0 | — |
| 4. | Drug resin complex | 70.0 | — |
| 5. | Polyvinyl pyrrolidone | 2.10 | 0.8 |
| 6. | Copovidone | 2.9 | 1.0 |
| 7. | Purified water | Q.s | — |
|  | Drug resin complex matrix | 74.98 | — |
| 8. | Drug resin complex matrix | 74.98 | — |
| 9. | Methacrylic acid copolymer | 34.1 | 12.17 |
| 10. | Methacrylic acid copolymer | 3.40 | 1.21 |
| 11. | Triethyl citrate | 3.75 | 1.33 |
| 12. | Talc | 18.75 | 6.69 |
| 13. | Isopropyl alcohol | Q.s | — |
| 14. | Purified water | Q.s | — |
|  | ER Coated particulates | 135.0 |  |
| 15. | ER Coated particulates | 135.0 | — |
| 16. | Donepezil HCl | 10.00 | 3.6 |
| 17. | Sodium carboxy methyl cellulose | 10.00 | 3.6 |
| 18. | Mannitol (Powder grade) | 64.7 | 23.1 |
| 19. | Polyacrylic acid (Carbopol 974P) | 12.0 | 4.3 |
| 20. | Talc | 5.00 | 1.8 |
| 21. | Sodium benzoate | 9.00 | 3.2 |
| 22. | Colloidal silicon dioxide | 10.00 | 3.6 |
| 23. | Iron oxide yellow | 0.30 | 0.1 |
| 24. | Sucralose | 3.00 | 1.1 |
| 25. | Orange flavour | 1.00 | 0.4 |
| 26. | Mannitol (Spray dried) | 20.00 | 7.1 |
|  | Powder for Suspension (per unit) | 280.0 mg | 100.0 |

Example 9

| S. NO. | Ingredients | mg/unit | Percentage |
|---|---|---|---|
| 1. | Memantine HCl | 28.0 | 9.33 |
| 2. | Sodium polystyrene sulfonate | 42.0 | 14.00 |
| 3. | Purified water | Q.s | Qs |
|  | Drug resin complex | 70.0 | — |

-continued

| S. NO. | Ingredients | mg/unit | Percentage |
|---|---|---|---|
| 4. | Drug resin complex | 70.0 | — |
| 5. | Polyvinyl pyrrolidone | 2.10 | 0.70 |
| 6. | Co-Povidone | 2.9 | 0.97 |
| 7. | Purified water | Q.s | — |
|  | Drug resin complex matrix | 74.98 | — |
| 8. | Drug resin complex matrix | 74.98 | — |
| 9. | Methacrylic acid copolymer | 34.1 | 11.37 |
| 10. | Methacrylic acid copolymer | 3.40 | 1.13 |
| 11. | Triethyl citrate | 3.75 | 1.25 |
| 12. | Talc | 18.75 | 6.25 |
| 13. | Isopropyl alcohol | Q.s | — |
| 14. | Purified water | Q.s | — |
|  | ER Coated particulates | 135.0 |  |
| 15. | ER Coated particulates | 135.0 | — |
| 16. | Donepezil HCl | 10.00 | 3.33 |
| 17. | Carboxy methyl cellulose | 10.00 | 3.33 |
| 18. | Talc | 5.00 | 1.67 |
| 19. | Sodium benzoate | 9.00 | 3.00 |
| 20. | Colloidal silicon dioxide | 10.00 | 3.33 |
| 21. | Iron oxide yellow | 0.30 | 0.10 |
| 22. | Sucralose | 3.00 | 1.00 |
| 23. | Orange flavor | 1.00 | 0.33 |
| 24. | Mannitol (Spray dried) | 40.00 | 13.33 |
| 25. | Mannitol (Powder grade) | 64.7 | 21.57 |
| 26. | Polyacrylic acid | 12.0 | 4.00 |
|  | Powder for Suspension (per unit) | 300.0 mg | 100.0 |

Manufacturing Process for Extended Release Oral Suspension Preparation:

The oral extended release suspension composition preparation includes the steps of:
  a) drug-resin complexation: memantine or its pharmaceutically acceptable salt was added to purified water in 1:22 ratio under stirring until clear solution obtained, sodium polystyrene sulfonate was added to obtained solution in 1:1.5 ratio under continuous stirring for 5 hours, filtered the dispersion through #400 mesh and rinsing with purified water to obtain drug-resin complex, drying was carried out to obtain dried drug-resin complex,
  b) drug-resin complex matrix preparation:
    i) polyvinyl pyrrolidone was added to the drug-resin complex in presence of granulating solvent by aqueous granulation or extrusion/spheronization once or till the required particle size is achieved for obtaining the drug-resin matrix granules I, drying was carried out to the obtain the dried granules, the dried granules were sifted through #40 mesh to obtain the desired size of the drug-resin matrix granules,
    ii) co-povidone was added to the obtained drug-resin matrix granules I and granulation is carried out in presence of granulating solvent by aqueous granulation or extrusion/spheronization once or till the required particle size is achieved for obtaining the drug-resin matrix granules II, the dried granules were sifted through #24 mesh to obtain the desired size of the drug-resin matrix granules,
  c) extended release coating: drug-resin matrix granules II obtained in step (b)(ii) were coated with the extended release coating system comprising methacrylic acid copolymer, plasticizer, anti-tacking agent and coating solvents till the uniform extended release coated drug-resin complex granules obtained, and
  d) powder for oral suspension preparation: blending the extended release coated drug resin complex granules II with pre-granulated sodium carboxy methyl cellulose and/or polyacrylic acid and mannitol passed through ASTM#20 mesh, mannitol (spray dried), and talc, and drying to obtain the dried granules, adding additional active ingredient directly either in powder form or granulated form with mannitol or polyacrylic acid in the extra-granular portion in blending step, further blending the obtained granules by adding sucralose, colloidal silicon dioxide, sodium benzoate and other pharmaceutically acceptable excipients.

I claim:

1. Oral extended release composition comprising memantine or its pharmaceutically acceptable salt using extended release resin complexation technology, wherein the composition comprising:
    (a) drug-resin complex comprising:
    5 to 15% (w/w) of Memantine or its pharmaceutically acceptable salt,
    5 to 25% (w/w) of sodium polystyrene sulfonate as resin complexation ingredient,
    (b) drug-resin complex matrix comprising:
    1 to 5% (w/w) of polyvinyl pyrrolidone or polyvinyl pyrrolidone and copovidone as release retardant,
    (c) extended release coating comprising:
    5 to 15% (w/w) of methacryclic acid copolymer as extended release coating polymer,
    0.1 to 3% (w/w) of triethyl citrate as plasticizing agent,
    1 to 8.5% (w/w) of talc as anti-tacking agent and
    (d) powder for oral suspension comprising:
    5 to 25% (w/w) of sodiumcarboxy methyl cellulose and/or polyacrylic acid as viscosity increasing agent,
    1 to 5% (w/w) of colloidal silicon dioxide as stabilizing agent,
    20 to 35% (w/w) of citric acid anhydrous or mannitol as diluent,
    1 to 5% (w/w) of talc as glidant,
    0.01 to 5% (w/w) of sucralose as sweetener,
    1 to 5% (w/w) of sodium benzoate as preservative,
    0.05 to 1.5% (w/w) of Iron oxide yellow as colorant,
    0.01 to 0.6% (w/w) of orange flavour as flavouring agent, and optionally
    1 to 15% (w/w) of other pharmaceutically acceptable excipient.

2. The oral extended release composition as claimed in claim 1, wherein the ratio of extended release coating polymer with respect to the active ingredient is in the range of 0.5:1 to 2.5:1, wherein the ratio of resin complexation ingredient with respect to the active ingredient is in the range of 1:1 to 3:1, wherein the ratio of release retardant with respect to the active ingredient in the range of 1:10 to 4:10, wherein the ratio of plasticizing agent with respect to the active ingredient in the range of 0.5:10 to 2:10, and wherein the ratio of anti-tacking agent with respect to the active ingredient in the range of 0.2:1 to 1.2:1.

3. The oral extended release composition as claimed in claim 1, wherein the memantine or its pharmaceutically acceptable salt is an active ingredient and pharmaceutically acceptable excipients, the oral extended release composition further comprising donepezil or its salt in the range of 5 mg to 23 mg as an additional active ingredient.

4. The oral extended release composition as claimed in claim 1, wherein the memantine or its pharmaceutically acceptable salt is an active ingredient and pharmaceutically acceptable excipients using extended release resin complexation technology, and wherein the composition is having drug-resin complex and matrix complex particles and coated drug-resin complex particles.

5. The oral extended release composition as claimed in claim 4, wherein the particle size of the drug-resin complex in the extended release composition ranges from 40 to 250 μm, the particle size of the drug-resin matrix complex in the extended release composition ranges from 50 to 450 μm, the particle size of the extended release coated drug-resinate matrix complex in the extended release composition ranges from 100 to 600 μm.

6. The oral extended release composition as claimed in claim 1, wherein the composition process of the preparation of memantine or its salt oral extended release composition comprising the steps of drug-resin complexation, matrix resinate/particulates preparation by aqueous granulation or extrusion/spheronization process followed by extended release coating, blending/ granulation and packing.

7. The oral extended release composition as claimed in claim 1, wherein the composition is prepared by a process comprising the steps of:
    (a) drug-resin complexation: adding Memantine or its pharmaceutically acceptable salt to purified water in 1:22 ratio under stirring until clear solution obtained, adding sodium polystyrene sulfonate to obtained solution in 1:1.5 ratio under continuous stirring for 5 hours, filter the dispersion through #400 mesh and rinsing with purified water to obtain drug-resin complex, drying the drug-resin complex,
    (b) drug-resin complex matrix preparation: granulating the obtained drug-resin complex by adding release retardant in presence of solvent by aqueous granulation or extrusion/spheronization once or till the required particle size is achieved for obtaining the drug-resin matrix complex, drying the obtained granules, sifting the dried granules through #40 mesh to obtain the desired size of the drug-resin matrix granules,
    (c) extended release coating: drug-resin matrix granules obtained from the step (b) are coated with extended release coating system comprising extended release water insoluble/swellable polymers, plasticizer, anti-tacking agent and coating solvents obtaining extended release coated drug-resin complex matrix granules, and
    (d) powder for oral suspension preparation: sifting extended release coated drug resin matrix particulates, pre-granulated viscosity increasing agents with diluents, glidants, sweeteners, stabilizing agents, preservatives and other pharmaceutically acceptable excipients, followed by blending to obtain powder for oral suspension.

* * * * *